United States Patent [19]

Schwarz et al.

[11] E Patent Number: Re. 32,146

[45] Reissued Date of Patent: May 13, 1986

[54] INSECT MATURATION INHIBITORS

[75] Inventors: Meyer Schwarz, Kensington; Richard W. Miller, Bowie, both of Md.; James E. Wright, Starkville, Miss.

[73] Assignee: The United States of America as represented by the Secretary of Agriculture, Washington, D.C.

[21] Appl. No.: 367,010

[22] Filed: Apr. 9, 1982

Related U.S. Patent Documents

Reissue of:

[64] Patent No.: 4,002,769
Issued: Jan. 11, 1977
Appl. No.: 599,731
Filed: Aug. 1, 1975

U.S. Applications:

[63] Continuation of Ser. No. 141,620, Apr. 18, 1980, abandoned, which is a continuation of Ser. No. 002,083, Jan. 9, 1979, abandoned, which is a continuation-in-part of Ser. No. 498,165, Aug. 16, 1974, abandoned.

[51] Int. Cl.[4] ..... A01N 31/00; A01N 31/14; A01N 33/18

[52] U.S. Cl. ..... 514/717; 514/712; 514/716; 514/718

[58] Field of Search ..... 424/339, 282, 337, 341; 514/712, 716, 717, 718

[56] References Cited

U.S. PATENT DOCUMENTS 3,825,661 7/1974 Emmick ..... 424/DIG. 12
3,873,724 3/1975 Beroza et al. ..... 424/DIG. 12

*Primary Examiner*—Allen J. Robinson
*Attorney, Agent, or Firm*—Oblon, Fisher, Spivak, McClelland & Maier

[57] ABSTRACT

Certain arylterpenoid compounds having excellent potential as insect control agents. The compounds are highly active as eclosion inhibiting agents against four species of flies and three species of mosquito.

2 Claims, No Drawings

INSECT MATURATION INHIBITORS

Matter enclosed in heavy brackets [ ] appears in the original patent but forms no part of this reissue specification; matter printed in italics indicates the additions made by reissue.

[This application is a continuation-in-part of application Ser. No. 498,165, filed Aug. 16, 1974, now abandoned.]

*This is a continuation, of application Ser. No. 141,620, filed Apr. 18, 1980, now abandoned which is a continuation of application Ser. No. 002,083, filed Jan. 9, 1979 now abandoned, which in turn is a reissue application of U.S. Pat. No. 4,002,769, which is a continuation-in-part of abandoned application Ser. No. 498,165 filed Aug. 16, 1974.*

This invention relates to certain arylterpenoid compounds useful in the control of insects and, more particularly, in the control of flies and mosquitoes.

A number of arylterpenoid compounds have exhibited juvenile hormone activity against several insect species as previously described by Schwarz et al. (Life Sci. 10, Part II, Biochem. Gen. Mol. Biol., 1125–1132, 1971 and J. Econ. Entomol., 67, 177–180, 1974). However, as the results described in the above two publications adequately demonstrate, one cannot use structural relationships to predict activity with even a modicum of reliability. For example, no correlation in activity was found between geometric isomers or between compounds in which the only structural difference was the position of the substituent on the aromatic portion of the molecule.

Consequently, it was unexpected and quite surprising when found that the arylterpenoid compounds of this invention having closely related structures display extremely high activity against several species of Diptera.

It is an object of this invention to provide compounds that inhibit the eclosion of adult flies and mosquitoes from pupae and interfere with insect development when applied directly to the insect larvae or pupae.

It is a further object of this invention to provide compounds that prevent emergence of insects from the larvae or pupae when they are applied to the natural growth media of the insects.

A further object of this invention is to provide compounds that inhibit the eclosion of flies and mosquitoes when they are incorporated in animal feces by feeding the compounds to cattle and other animals.

A still further object of this invention is to provide compounds that inhibit the eclosion of flies and mosquitoes when sprayed in appropriate animal housing areas.

The compounds of this invention have the following structural formula:

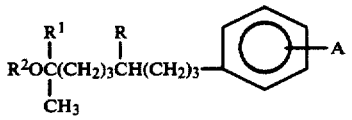

in which A is alkyl having 1 to 5 carbon atoms, preferably ethyl isopropyl or sec.-butyl; alkoxy having 1 to 4 carbon atoms; alkylthio having 1 to 4 carbon atoms; nitro or 3,4-methylene dioxy; more preferably A is in the para position and most preferably A is in the para position and is alkyl having 1 to 5 carbon atoms; R and $R^1$ are independently methyl or ethyl, preferably methyl; and $R^2$ is alkyl having 1 to 4 carbon atoms, preferably methyl or ethyl, more preferably methyl. The compounds will inhibit eclosion of flies and mosquitoes when applied in a variety of ways including application directly to the insect larvae or pupae, application to the natural growth media such as animal feces, incorporation of the compounds in the diets of livestock and poultry and by spray application in appropriate animal housing areas.

This invention is particularly concerned with the preparation and activity of the arylterpenoid compounds against the house fly, Musca domestica (L.); the face fly, Musca autumnalis DeGeer; the stable fly, Stomoxys calcitrans (L.); the horn fly, Haematobia irritans (L.); and the mosquito, Anopheles quadrimaculatus. The structure and names of several compounds are listed in Table 1. All of these compounds were tested by applying them directly to the insect papae while some of them were tested by feeding to cattle and by spraying the compounds on rearing pans containing artificial insect growth media. In general, the compounds of this invention can be prepared according to the following outline.

Scheme 1
Preparation of arylterpenoid compounds

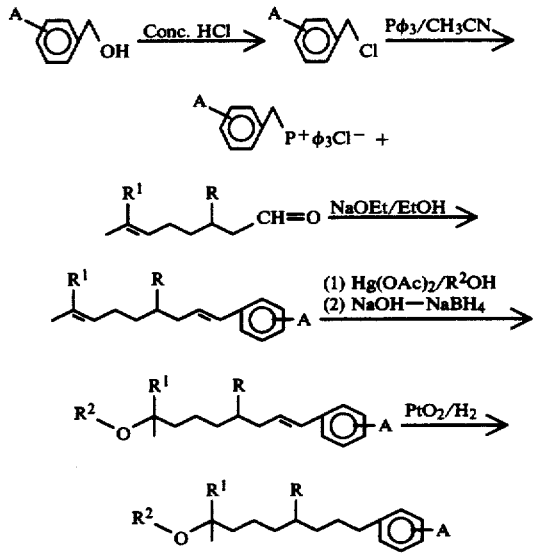

wherein A, R, $R^1$ and $R^2$ are as defined.

wherein A, R, $R^1$ and $R^2$ are as defined.

The benzyl alcohols used as starting materials are freed of contaminating ortho isomers by spinning band distillation. The chlorides and triphenylphosphonium salts are prepared in the usual manner and are obtained in nearly quantitative yields. The Wittig reactions (Organic Reactions, Vol. 14, pages 270–490, John Wiley and Sons, Inc., New York, 1965) are carried out in absolute ethanol with sodium ethoxide as the base and yield 80% of a 60:40 mixture of Z and E isomers. The alkoxymercuration-demercuration reaction is carried out in 80–90% yields by using the appropriate alcohol ($R^2OH$) as the solvent (J. Med. Chem., 12, 191–192, 1969). The remaining double bond was hydrogenated at atmospheric pressure with $PtO_2$ as the catalyst.

In order to illustrate a typical preparation, the following is a detailed example of the preparation of compound 4 in Table 1.

PREPARATION OF COMPOUND 4 p-Isopropylbenzylchloride p-Isopropylbenzyl alcohol (128 g., 0.85 mol.) was added dropwise with stirring to 400 ml of concentration HCl, while the temperature was kept between 25° and 30° C. The reaction mixture was stirred for 4 hours and worked up by pouring into 500 ml of ice water and extracting with hexane. The hexane extracts were washed to neutrality yielding 135 g. (93%) of p-Isopropylbenzylchloride, bp 108° C/18 mm. $n_D^{25}=1.5212$ p-Isopropylbenzyltriphenylphosphonium chloride p-Isopropylbenzylchloride (168.5 g, 1 mol.) and triphenylphosphine (275 g, 1.05 mol.) were refluxed overnight in acetonitrile (600 ml). Approximately 300 ml of acetonitrile were removed in vacuo and 500 ml ether was added. The salt was allowed to crystallize and the salt was filtered off and washed with ether. Yield of the first crop of crystals was 388 g (90%) of desired salt. Some additional salt could be recovered from the mother liquors.

4,8-Dimethyl-1-(p-isopropylphenyl)-nona-1,7-diene

To a stirred solution of sodium (21 g, 0.9 at) in 1500 ml of absolute ethanol was added 388 g of p-isopropylbenzyltriphenylphosphonium chloride. The resulting phosphorane solution was cooled to 15°-20° C. (The light orange color fades when the temperature is lowered!) Freshly vacuum distilled citronellal (150 g, 1 mol.) was added dropwise while keeping the reaction mixture at reflux for 4 hours. The cooled reaction mixture was filtered to remove sodium chloride, most of the alcohol was distilled off in vacuo and 500 ml of hexane was added. The triphenylphosphineoxide was allowed to crystallize and filtered off. The solvents were removed from the mother liquors under vacuum and another 500 ml of hexane added. Cooling afforded another crop of triphenylphosphineoxide. The hexane was again evaporated and the residue distilled yielding, after a small forerun of isopulegol (a contaminant of citronellal), 200 g (82%) of the desired product. bp. 150°-145° C/0.1 mm. Ratio of E to Z is app. 40:60. $n_D^{25}=1.5172$.

4,8-Dimethyl-1-(p-Isopropylphenyl)-non-1-ene

To a stirred solution of 16 g (0.7 g at) of sodium in 600 ml of liquid ammonia was added dropwise a solution of 93 g (0.34 mol.) of 4,8-dimethyl-1-(p-isopropylphenyl)-nona-1,7-diene in 125 ml of anhydrous tetrahydrofuran. Total addition time was one hour. The excess sodium was destroyed by the cautious addition of methanol. Then 200 ml of hexane were added and the ammonia was allowed to evaporate. To the residue a saturated solution of $NH_4Cl$ was added cautiously. The organic layer was separated, and the aqueous layer was diluted with water and extracted twice with hexane. The combined hexane layers were washed with water, dilute HCl, brine and then dried. Evaporation of the hexane and distillation of the residue yielded the title product. Yield was 88 g (94%), bp 130°-135° C/0.1 mm. $n_D^{25}=1.4938$.

2-Ethoxy-9-(p-Isopropylphenyl)1-2,6-Dimethylnonane

To a stirred solution of 27 g (0.1 mole) of 4,8-dimethyl-1-(p-isopropylphenyl)-non-1-ene in 125 ml absolute ethanol was added portionwise at room temperature 34 g (0.11 mole) of mercuric acetate. The mixture was stirred for 1 hour, at which time all mercuric acetate had dissolved. Then the reaction mixture was cooled to 5° and 15 g of NaOH in 100 ml 80% ethanol was added dropwise, keeping the reaction mixture below 25° C. Then 3.5 g of $NaBH_3$ was added portionwise, again keeping the mixture below 25° C. Hexane (200 ml) and 200 ml water were then added, and mixture stirred until the mercury had coagulated. The organic layer separated and the aqueous layer extracted with two 100 ml portions of hexane. The combined hexane layers were extracted with water, dilute HCl, water and brine. The organic layer was then dried and the hexane removed in vacuo. The residue was distilled at 145° C/01 mm to yield 28.5 g (90%) of title compound. $n_D^{25}=1.4806$.

Activity of the compounds against face and house flies was determined by the procedure of Miller et al (J. Econ. Entomol. 63, 853-855. 1970) and activity against horn flies was determined by the procedure of Harris et al (J. Econ. Entomol. 66, 1099-1102, 1973). Essentially, these procedures involve seeding day old larvae or eggs in either fresh cattle feces or in an artificial medium that contained the compound being tested. The results are shown in Table 2. Activity of the compounds against stable and house flies was also determined by topical application of an acetone solution of the compound being tested by newly ecdysed pupae as described in J. Econ. Entomol, 65, 1361-1364, 1972.

Compounds 2 and 4 in Table 1 were further tested by feeding them to cattle and seeding fly larvae or eggs in the feces of the thus treated cattle. Face and house fly larvae were seeded in the feces of the treated cattle and tested according to the procedures of Miller and Uebel (J. Econ. Entomol., 67, 69-70, 1974), while stable and horn fly eggs were seeded in the feces of the treated cattle and tested according to the procedures of Harris et al (J. Econ. Entomol., 66, 1099-1102, 1973). The results of these feeding tests are shown in Table 3.

Spray tests were also conducted according to the procedure described by Wright (J. Econ. Entomol., 65, 1361-1364, 1972). An appropriate quantity of an emulsifiable concentrate containing 25 parts of the candidate compound, 65 parts of xylene, and 10 parts of a nonionic surfactant, octyl phenoxy polyethoxy ethanol (Triton X-100) in 100 ml of water was sprayed on rearing pans containing artificial media and four-day old house fly larvae or six-day old stable fly larvae. The rearing pans were then placed in screened cages for adult eclosion. The eclosed adults were counted 14 days after the treatment and percentage inhibition of eclosion determined.

As shown in Table 2, the tested compounds of this invention had very high activity against the face fly when tested by seeding larvae or eggs in the natural growth media of the flies by the method set forth above. Compounds 1 and 2 exhibited high activity against the horn fly. Since the face fly is generally more resistant than the horn fly to the activity of maturation inhibiting compounds and since compounds 3 and 4 had shown high activity against the face fly, they were not tested against the horn fly.

Among the four species of flies used for the purpose of this invention, the generally established order of susceptability to the action of maturation inhibiting compounds is, from most resistant to least resistant, house fly, face fly, stable fly, and horn fly. Of course, exceptions to this general order occasionally occur.

Topical application in acetone solution of from 0.1 to 0.01 μg of each of the six compounds to stable and house fly pupae sufficed to prevent eclosion.

The results of the feeding tests with compounds 2 and 4 are shown in Table 3. In these tests, cattle were fed for a week, but the manure for test purpose was collected only on the last 5 days of the feeding week. Compound 4 exhibited the most activity against all four fly species.

Both compounds 2 and 4 exhibited excellent activity in the spray tests, especially at application rates of 10 mg/sq ft and higher. The results are shown in Table 4.

In addition to activity against the four species of flies, the recited compounds of this invention were tested and exhibited remarkable activity against the mosquito, Amopheles quadrimaculatus and the other two species indicated. The very low LC-50, that is, the concentration (lethal concentration) in water that inhibits eclosion of 50% of the mosquito pupae, of compounds 3 and 4 is considered especially remarkable by skilled workers in the field of insects affecting man. The results are shown in Tables 5 and 6. The testing procedure used is a routine method and is generally described in Mosquito News 31, 540–543, 1971.

The activity of the compounds of this invention against flies and mosquitoes was very surprising because when they were tested against conventional screening insects, T. molitor and O. fasciatus, they exhibited extremely low activity. In fact, compound 4 showed no activity whatsoever, and the other compounds showed, at best, only moderate activity. This is important to note because usually when compounds or other materials are screened against T. molitor and O. fasciatus and found not active or only slightly active, they are not considered worth testing against other insects because these two screening insect species are more susceptible to juvenile hormone type materials than most other insects. Consequently, the remarkably high activity of the compounds of this invention against the four species of flies and against the three species of mosquito was completely unpredicted and unexpected.

TABLE 1

| Compound number | Structures and names of arylterpenoid compounds | |
|---|---|---|
| 1 | 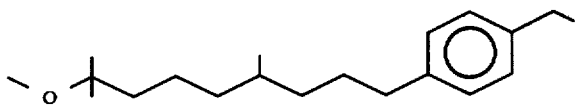 | 2-methoxy-9-(p-ethylphenyl)-2,6-dimethylnonane |
| 2 | 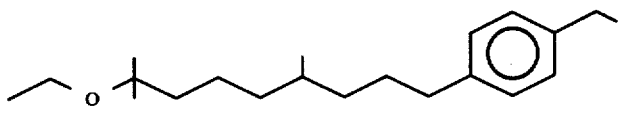 | 2-ethoxy-9-(p-ethylphenyl)-2,6-dimethylnonane |
| 3 | 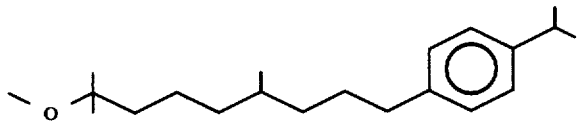 | 2-methoxy-9-(p-isopropylphenyl)-2,6-dimethylnonane |
| 4 | 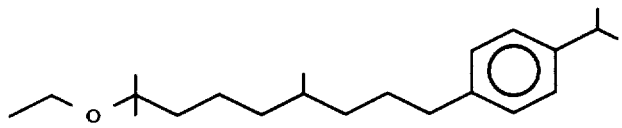 | 2-ethoxy-9-(p-isopropylphenyl)-2,6-dimethylnonane |
| 5 | 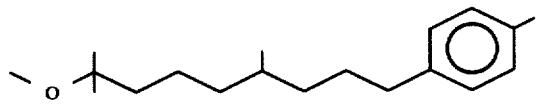 | 2-methoxy-9-(p-methylphenyl)-2,6-dimethylnonane |
| 6 | 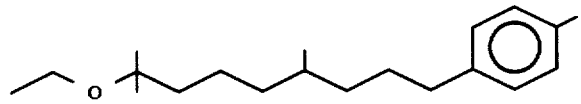 | 2-ethoxy-9-(p-methylphenyl)-2,6-dimethylnonane |
| 7 | 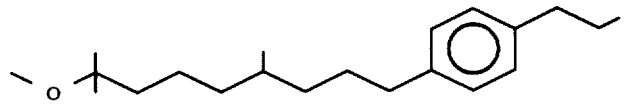 | 2-methoxy-9-(p-n-propylphenyl)-2,6-dimethylnonane |
| 8 | 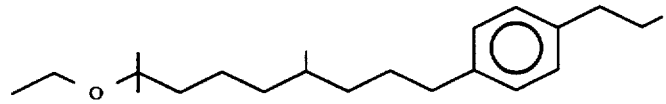 | 2-ethoxy-9-(p-n-propylphenyl)-2,6-dimethylnonane |

TABLE 1-continued

| Compound number | Structures and names of arylterpenoid compounds | |
|---|---|---|
| 9 | 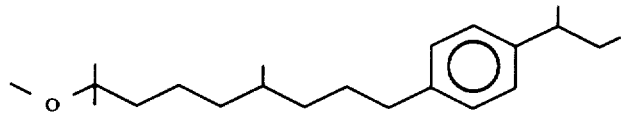 | 2-methoxy-9-(p-sec. butylphenyl)-2,6-dimethylnonane |
| 10 | 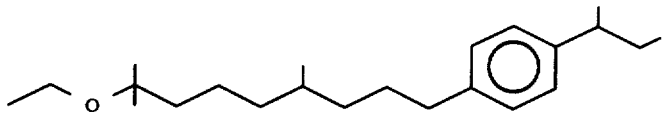 | 2-ethoxy-9-(p-t-sec. butylphenyl)-2,6-dimethylnonane |
| 11 | 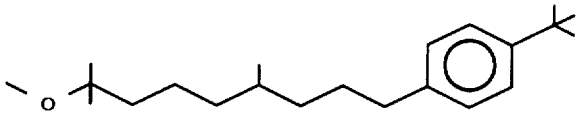 | 2-methyl-9-(p-t-butylphenyl)-2,6-dimethylnonane |
| 12 | 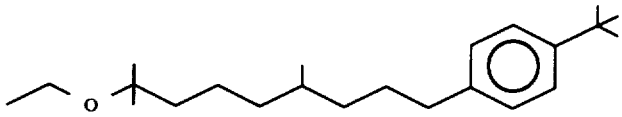 | 2-ethoxy-9-(p-t-butylphenyl)-2,6-dimethylnonane |

TABLE 2

Juvenile hormone activity of arylterpenoid compounds incorporated in the natural growth media of flies

| Compound | Dosage (ppm) | % inhibition of eclosion of adults[a] from pupae | | |
|---|---|---|---|---|
| | | Face fly | House fly | Horn fly |
| 1 | 0.1 | | | 93 |
| | 1.0 | 94 | 37 | 100 |
| | 5.0 | 100 | 73 | |
| | 10.0 | 100 | 89 | 100 |
| 2 | 0.1 | | | 55 |
| | 1.0 | 95 | 61 | 95 |
| | 5.0 | 98 | 77 | |
| | 10.0 | 100 | 88 | 100 |
| 3 | 0.1 | 100 | 12 | |
| | 1.0 | 100 | 87 | |
| | 5.0 | 100 | 100 | |
| | 10.0 | 100 | 97 | |
| 4 | 0.1 | 84 | 8 | |
| | 1.0 | 100 | 72 | |
| | 5.0 | 98 | 100 | |
| | 10.0 | 100 | 100 | |
| 5 | 0.1 | | | |
| | 1.0 | 39 | 12 | |
| | 5.0 | | | |
| | 10.0 | 40 | 0 | |
| 6 | 0.1 | | | |
| | 1.0 | 44 | 14 | |
| | 5.0 | | | |
| | 10.0 | 100 | 88 | |
| 7 | 0.1 | | | |
| | 1.0 | | | |
| | 5.0 | | | |
| | 10.0 | 90 | 79 | |
| 8 | 0.1 | | | |
| | 1.0 | | | |
| | 5.0 | | | |
| | 10.0 | 88 | 63 | |
| 9 | 0.1 | | | |
| | 1.0 | 100 | 54 | |
| | 5.0 | | | |
| | 10.0 | 100 | 95 | |
| 10 | 0.1 | | | |
| | 1.0 | 100 | 26 | |
| | 5.0 | | | |
| | 10.0 | 100 | 99 | |
| 11 | 0.1 | | | |
| | 1.0 | | | |
| | 5.0 | | | |

TABLE 2-continued

Juvenile hormone activity of arylterpenoid compounds incorporated in the natural growth media of flies

| Compound | Dosage (ppm) | % inhibition of eclosion of adults[a] from pupae | | |
|---|---|---|---|---|
| | | Face fly | House fly | Horn fly |
| | 10.0 | 4 | 1 | |
| 12 | 0.1 | | | |
| | 1.0 | | | |
| | 5.0 | | | |
| | 10.0 | 28 | 10 | |

[a]Adjusted for control inhibition by Abbott's formula, J. Econ. Entomol., 18,265-7, 1925.

TABLE 3

Development of face flies, house flies, stable flies, and horn flies in feces from cattle fed 3 arylterpenoid compounds.

| Compound | Dosage (mg/kg) body wt/day) | % Inhibition of adult eclosion from pupae[a] | | | |
|---|---|---|---|---|---|
| | | Face fly | House fly | Stable fly | Horn fly |
| 2 | 2.5 | 100 | 80 | | |
| | 1.25 | | | 100 | 100 |
| | 1.0 | 100 | 65 | | |
| | 0.5 | 88 | 38 | 100 | 79 |
| | 0.25 | 59 | 19 | | 82[b] |
| | 0.125 | 0 | 1 | | |
| 3 | 0.5 | 100 | 68 | | |
| | 0.25 | 100 | 61 | | |
| | 0.125 | 99 | 42 | | |
| 4 | 2.5 | 100 | 95 | | |
| | 1.25 | | | | |
| | 1.0 | 100 | 95 | | |
| | 0.5 | 100 | 64 | 100 | 100 |
| | 0.25 | 100 | 54 | 100[b] | 100[b] |
| | 0.125 | 97 | 20 | 50[c] | 95[c] |

[a]Adjusted for control inhibition by Abbott's formula, J. Econ. Entomol., 18, 265-267, 1925.

[b]Concentrations obtained by diluting 1 pt feces from cattle fed at a rate of 0.5 mg with 1 pt of control feces.

[c]Concentrations obtained by diluting 1 pt feces from cattle fed at a rate of 0.5 mg with 3 pt of control feces.

TABLE 4

Development of stable fly and house fly from medium treated by surface sprays of 3 arylterpenoid compounds.

| Rate of application (mg/ft²) | % inhibition of stable fly and house fly eclosion due to treatment with indicated compound | | | | | |
|---|---|---|---|---|---|---|
| | 1 | | 3 | | 6 | |
| | Stable fly | House fly | Stable fly | House fly | Stable fly | House fly |
| 500 | 100 | 100 | 100 | 99 | 100 | 100 |
| 250 | 100 | 100 | 100 | 99 | 100 | 100 |
| 100 | 100 | 99 | 100 | 99 | 100 | 100 |
| 40 | 100 | 100 | 100 | 97 | 100 | 100 |
| 20 | 100 | 100 | 100 | 77 | 99 | 100 |
| 10 | 100 | 100 | 100 | 72 | 99 | 97 |
| 5 | 90 | 87 | 90 | 43 | 81 | 43 |
| 1 | 58 | 54 | 3 | 38 | 71 | |
| 0.5 | 8 | 11 | | | 65 | |
| 0.1 | | | | | 20 | |

TABLE 5

Development inhibiting activity of arylterpenoid compound against *Anopheles quadrimaculatus*

| Compound | Amount of compound needed to obtain indicated lethal concentration | |
|---|---|---|
| | LC-50 (ppm) | LC-90 (ppm) |
| 1 | 0.0014 | 0.0061 |
| 2 | 0.0035 | 0.0245 |
| 3 | 0.0004 | 0.0015 |
| 4 | 0.0004 | 0.0024 |

TABLE 6

Developmental inhibiting acitvity of arylterpenoid compound against *Anopheles quadrimaculatus*, *Anopheles albimanus* and *Aedes taeniorhynchus*

| Compound | Amount of compound needed to obtain indicated lethal concentration $LC_{90}$ in p.p.m. | | |
|---|---|---|---|
| | *Anopheles quadrimaculatus* | *Anopheles albimanus* | *Aedes taeniorhynchus* |
| 1 | 0.0061 | 0.0140 | 0.0011 |
| 2 | 0.0245 | 0.0216 | 0.0014 |
| 3 | 0.0019 | 0.0005 | 0.0007 |
| 4 | 0.0024 | 0.0005 | 0.0009 |

We claim:

[1. A method of inhibiting the eclosion of fly pupae comprising adding to the natural growth media of said pupae from about 0.1 to about 10.0 ppm of a compound of the general formula:

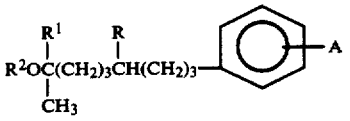

in which A is alkyl having 1 to 5 carbon atoms, alkoxy having 1 to 4 carbon atoms, alkylthio having 1 to 4 carbon atoms, or nitro; R and $R^1$ are independently methyl or ethyl; and, $R^2$ is alkyl having 1 to 4 carbon atoms.]

[2. The method of claim 1 in which A is in the para position.]

[3. The method of claim 1 in which the pupae is that of flies selected from the species consisting of the face fly, the house fly and the horn fly.]

[4. The method of claim 3 in which the compound is selected from the group of consisting of 2-methoxy-9-(p-ethylphenyl)-2,6-dimethylnonane; 2-ethoxy-9-(p-ethylphenyl)-2,6-dimethylnonane; 2-methoxy-9-(p-isopropylphenyl)-2,6-dimethylnonane; 2-ethoxy-9-(p-isopropylphenyl)-2,6-dimethylnonane; 2-methoxy-9-(p-sec.-butylphenyl)-2,6-dimethylnonane; and, 2-ethoxy-9-(p-sec.-butylphenyl)-2,6-dimethylnonane.]

[5. A method of inhibiting the eclosion of fly puypae comprising feeding to cattle from about 0.125 mg to about 2.5 mg per kilogram of body weight per day of a compound of the general formula:

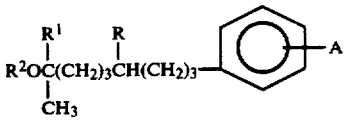

in which A is alkyl having 1 to 5 carbon atoms, alkoxy having 1 to 4 carbon atoms, alkylthio having 1 to 4 carbon atoms, or nitro; R and $R^1$ are independently methyl or ethyl; and, $R^2$ is alkyl having 1 to 4 carbon atoms; said feeding serving to incorporate an eclosion inhibiting amount of said compound in a natural growth media, cattle feces, of the fly pupae.]

[6. The method of claim 5 in which A is in the para position.]

[7. The method of claim 5 in which the pupae is that of flies selected from the species consisting of the face fly, the house fly, the stable fly and the horn fly.]

[8. The method of claim 7 in which the compound is selected from the group consisting of 2-ethoxy-9-(p-ethylphenyl)-2,6-dimethylnonane and 2- ethoxy-9-(p-isopropylphenyl)-2,6-dimethylnonane.]

[9. A method of inhibiting the eclosion of fly pupae comprising spraying the growth media of said pupae with an emulsifiable concentration containing about 25% of a compound of the general formula:

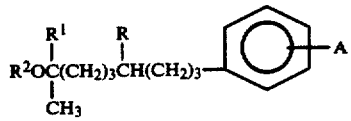

in which A is alkyl having 1 t 5 carbon atoms, alkoxy having 1 to 4 carbon atoms, alkylthio having 1 to 4 carbon atoms, or nitro; R and $R^1$ are independently methyl or ethyl; and, $R^2$ is alkyl having 1 to 4 carbon atoms; said compound being applied to the growth media at a rate of from 5 to 500 mg per square foot.]

[10. The method of claim 9 in which A is in the para position.]

[11. The method of claim 9 in which the pupae is that of flies selected from the group consisting of the stable fly and the house fly.]

[12. The method of claim 11 in which the compound is selected from the group consisting of 2-ethoxy-9-(p-ethylphenyl)-2,6-dimethylnonane and 2-ethoxy-9-(p-isopropylphenyl)-2,6-dimethylnonane.]

[13. A method of inhibiting the eclosion of pupae of the mosquito, Anopheles quadrimaculatus, comprising applying to the growth media of said mosquito an eclosion inhibiting amount of a compound of the general formula:

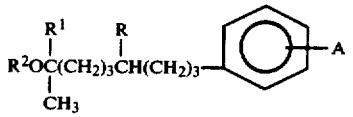

in which A is alkyl having 1 to 5 carbon atoms, alkoxy having 1 to 4 carbon atoms, alkylthio having 1 to 4 carbon atoms, or nitro; R and $R^1$ are independently methyl or ethyl; and, $R^2$ is alkyl having 1 to 4 carbon atoms.]

[14. The method of claim 13 in which A is in the para position.]

[15. The method of claim 13 in which from about 0.0004 ppm to about 0.0245 ppm of the compound is applied to the growth media.]

[16. The method of claim 15 in which the compound is selected from the group consisting of 2-methoxy-9-(p-ethylphenyl)-2,6-dimethylnonane; 2-ethoxy-9-(p-ethylphenyl)-2,6-dimethylnonane; 2-methoxy-9-(p-isopropylphenyl)-2,6-dimethylnonane; and, 2-ethoxy-9-(p-isopropylphenyl)-2,6-dimethylnonane.]

*17. An insecticidally active composition which is effective against insect pupae, comprising:*

*an insecticidally effective amount of a compound selected from the group consisting of 2-methoxy-9-(p-ethylphenyl)-2,6-dimethylnonane, 2-ethoxy-9-(p-ethylphenyl)-2,6-dimethylnonane, 2-methoxy-9-(p-isopropylphenyl)-2,6-dimethylnonane, and 2-ethoxy-9-(p-isopropylphenyl)-2,6-dimethylnonane supported on an inert diluent carrier, said pupae being susceptible to maturation inhibition by said compound.*

*18. The composition of claim 17, wherein said compound is 2-methoxy-9-(p-isopropylphenyl)-2,6-dimethylnonane.*

* * * * *